United States Patent [19]

Schaefer et al.

[11] Patent Number: 5,380,657
[45] Date of Patent: Jan. 10, 1995

[54] METHOD FOR ISOLATION OF INSERTION ELEMENTS FROM CORYNEFORM BACTERIA

[75] Inventors: Andreas Schaefer; Anna-Hildegard Seep-Feldhaus; Wolfgang Jaeger; Joern Kalinowski; Wolfgang Wohlleben; Alfred Puehler, all of Bielefeld, Germany

[73] Assignee: Degussa Aktiengesellschaft, Frankfurt, Germany

[21] Appl. No.: 33,320

[22] Filed: Mar. 18, 1993

[30] Foreign Application Priority Data

Mar. 19, 1992 [DE] Germany ................. 4208785

[51] Int. Cl.$^6$ ............................................. C12N 15/11
[52] U.S. Cl. ......................... 435/172.3; 435/252.32; 435/320.1
[58] Field of Search ................ 435/5, 172.3, 252.32, 435/320.1

[56] References Cited

FOREIGN PATENT DOCUMENTS

| 46086/89 | 6/1990 | Australia . |
| 2037431 | 3/1991 | Canada . |
| 0252558 | 1/1988 | European Pat. Off. . |
| 0372230 | 6/1990 | European Pat. Off. . |
| 0445385 | 9/1991 | European Pat. Off. . |
| WO91/00913 | 1/1991 | WIPO . |

OTHER PUBLICATIONS

Boehringer Mannheim GmbH Biochemica, *DNA Labeling and Detection Nonradioactive*, 1989.
Gay, P., et al., "Positive Selection Procedure for Entrapment of Insertion Sequence Elements in Gram-negative Bacteria", Journal of Bacteriology, Nov. 1985, pp. 918–921.
Jager, W. et al., "Expression of the *Bacillus subtilis* sacβ Gene Leads to Sucrose Sensitivity in the Gram-Positive Bacterium *Corynebacterium glutamicum* but Not in *Streptomyces*", Journal of Bacteriology, Aug., 1992, pp. 5462–5465.

*Primary Examiner*—Richard A. Schwartz
*Assistant Examiner*—Gary L. Brown
*Attorney, Agent, or Firm*—Beveridge, DeGrandi, Weilacher & Young

[57] ABSTRACT

A method locating insertion elements (IS elements) or transposons in coryneform bacteria, a positive selection system suitable for the above, the IS elements found in this manner and their use, is disclosed. The method involves:

(1) The construction of a non-self-transferrable vector mobilizable from an *E. coli* mobilizer strain which vector is composed of
  (a) A DNA segment containing a replicon functional in *E. coli*,
  (b) A second DNA segment containing the DNA fragment coding for the mobilization function (Mob site containing the oriT),
  (c) A third DNA segment which recombines homologously in Gram-positive bacteria and/or contains a replicon functional in coryneform bacteria,
  (d) A DNA segment from *Bacillus subtilis* containing the sacB gens,
(2) Transfer of this vector by means of conjugative transfer into the coryneform recipient strains,
(3) Cultivation of the transconjugants containing the vector in an ~10% sucrose-containing nutrient medium,
(4) Lysis of the sucrose-resistant clones, cleaving of the plasmids with restriction endonucleases and analysis of the fragments.

4 Claims, 5 Drawing Sheets

```
                 GGCCCTTCCGGTTTTGGGGTACATCACAGAACCTGGGCTAGCGGTGTAGACCCGAAAATA
                     10        20        30        40        50        60
                 AACGAGCCTTTTGTCAGGGTTAAGGTTTAGGTATCTAAGCTAACCAAACACCAACAAAAG
                     70        80        90        100       110       120
                        M  K  S  T  G  N  I  I  A  D  T  I  C  R  T  -  E
                 GCTCTACCCATGAAGTCTACCGGCAACATCATCGCTGACACCATCTGCCGCACTNGCGAA
                     130       140       150       160       170       180
                     L  G  L  T  I  T  G  A  S  D  A  G  D  Y  T  L  I  E  A  D
                 CTAGGACTCACCATCACCGGCGCTTCCGATGCAGGTGATTACACCCTGATCGAAGCAGAC
                     190       200       210       220       230       240
                     A  L  D  Y  T  S  T  C  P  E  C  S  Q  P  G  V  F  R  H  H
                 GCACTCGACTACACCTCCACCTGCCCAGAATGCTCCCAACCTGGGGTGTTTCGTCATCAC
                     250       260       270       280       290       300
                     T  H  R  M  L  I  D  L  P  I  V  G  F  P  P  N  C  L  S  V
                               F  T  H  R  R  V  S  T  K  L  F  I  R  L
                 ACCCACCGGATGCTCATTGATTTACCCATCGTCGGGTTTCCACCAAACTGTTTATCCGTC
                     310       320       330       340       350       360
                     Y  L  A  T  A  A  P  T  P  H  V  S  K  S  I  S  K  Q  N  *
                     P  R  Y  R  C  T  N  P  T  C  K  Q  K  Y  F  Q  A  E  L  S
                 TACCTCGCTACCGCTGCACCAACCCCACATGTAAGCAAAAGTATTTCCAAGCAGAACTAA
                     370       380       390       400       410       420
                        C  A  D  H  G  K  K  V  T  H  R  V  T  R  W  I  L  Q  R  L
                 GCTGCGCTGACCACGGTAAAAAGGTCACCCACCGGGTCACCCGCTGGATTTTACAACGCC
                     430       440       450       460       470       480
                         A  I  D  R  M  S  V  H  A  T  A  K  A  L  G  L  G  W  D  L
                 TTGCTATTGACCGGATGAGTGTTCACGCAACCGCGAAAGCACTTGGGCTAGGGTGGGATT
                     490       500       510       520       530       540
                      T  C  Q  L  A  L  D  M  C  R  E  L  V  Y  N  D  P  H  H  L
                 TAACCTGCCAACTAGCCCTCGATATGTGCCGTGAGCTGGTCTATAACGATCCTCACCATC
                     550       560       570       580       590       600
                     D  G  V  Y  V  I  G  V  D  E  H  K  W  S  H  N  R  A  K  H
                 TTGATGGAGTGTATGTCATTGGGGTGGATGAGCATAAGTGGTCACATAATAGGGCTAAGC
                     610       620       630       640       650       660
                     G  D  G  F  V  T  V  I  V  D  M  T  G  H  R  Y  D  S  R  C
                 ATGGTGATGGGTTTGTCACCGTGATTGTCGATATGACCGGGCATCGGTATGACTCACGGT
                     670       680       690       700       710       720
                     P  A  R  L  L  D  V  V  P  G  R  S  A  D  A  L  R  S  W  L
                 GTCCTGCCCGGTTATTAGATGTCGTCCCAGGTCGTAGTGCTGATGCTTTACGGTCCTGGC
                     730       740       750       760       770       780
                     G  S  R  G  E  Q  F  R  N  Q  I  R  I  V  S  M  D  G  F  Q
                 TTGGCTCCCGCGGTGAACAGTTCCGCAATCAGATACGGATCGTGTCCATGGATGGATTCC
                     790       800       810       820       830       840
```

FIG. 2/1

```
        G  Y  A  T  A  S  K  E  L  I  P  S  A  R  R  V  M  D  P  F
    AAGGCTACGCCACAGCAAGTAAAGAACTCATTCCTTCTGCTCGTCGCGTGATGGATCCAT
        850       860       870       880       890       900

H  V  V  R  L  A  G  D  K  L  T  A  C  R  Q  R  L  Q  R  E
    TCCATGTTGTGCGGCTTGCTGGTGACAAGCTCACCGCCTGCCGGCAACGCCTCCAGCGGG
        910       920       930       940       950       960

K  Y  Q  R  R  G  L  S  Q  D  P  L  Y  K  N  R  K  T  L  L
    AGAAATACCAGCGTCGTGGTTTAAGCCAGGATCCGTTGTATAAAAACCGGAAGACCTTGT
        970       980       990       1000      1010      1020

T  T  H  K  W  L  S  P  R  Q  Q  E  S  L  E  Q  L  W  A  Y
    TGACCACGCACAAGTGGTTGAGTCCTCGTCAGCAAGAAAGCTTGGAGCAGTTGTGGGCGT
        1030      1040      1050      1060      1070      1080

D  K  D  Y  G  A  L  K  L  A  W  L  A  Y  Q  A  I  I  D  C
    ATGACAAAGACTACGGGGCGTTAAAGCTTGCGTGGCTTGCGTATCAGGCGATTATTGATT
        1090      1100      1110      1120      1130      1140

Y  Q  M  G  N  K  R  E  A  K  K  K  M  R  T  I  I  D  Q  L
    GTTATCAGATGGGTAATAAGCGTGAAGCGAAGAAGAAAATGCGGACCATTATTGATCAGC
        1150      1160      1170      1180      1190      1200

R  V  L  K  G  P  N  K  E  L  A  Q  L  G  R  S  L  F  K  R
    TTCGGGTGTTGAAGGGGCCGAATAAGGAACTCGCGCAGTTGGGTCGTAGTTTGTTTAAAC
        1210      1220      1230      1240      1250      1260

L  G  D  V  L  A  Y  F  D  V  G  V  S  N  G  P  V  E  A  I
    GACTTGGTGATGTGTTGGCGTATTTCGATGTTGGTGTCTCCAACGGTCCGGTCGAAGCGA
        1270      1280      1290      1300      1310      1320

N  G  R  L  E  H  L  R  G  I  A  L  G  F  R  N  L  N  H  Y
    TCAACGGACGGTTGGAGCATTTGCGTGGGATTGCTCTAGGTTTCCGTAATTTGAACCACT
        1330      1340      1350      1360      1370      1380

I  L  R  C  L  I  H  S  G  Q  L  V  H  K  I  N  A  L  *
    ACATTCTGCGGTGCCTTATCCATTCAGGGCAGTTGGTCCATAAGATCAATGCACTCTAAA
        1390      1400      1410      1420      1430      1440

ACAGGAAGAGCC
        1450
```

FIG. 2/2

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1452 base pairs
        ( B ) TYPE: nucleic acid
        ( C ) STRANDEDNESS: single
        ( D ) TOPOLOGY: unknown (i i) MOLECULE TYPE: DNA (genomic)

(x i) SEQUENCE DESCRIPTION: SEQ ID NO:1:

| | | | | | |
|---|---|---|---|---|---|
| GGCCCTTCCG | GTTTTGGGGT | ACATCACAGA | ACCTGGGCTA | GCGGTGTAGA | CCCGAAAATA | 60
| AACGAGCCTT | TTGTCAGGGT | TAAGGTTTAG | GTATCTAAGC | TAACCAAACA | CCAACAAAAG | 120
| GCTCTACCCA | TGAAGTCTAC | CGGCAACATC | ATCGCTGACA | CCATCTGCCG | CACTGCGAAC | 180
| TAGGACTCAC | CATCACCGGC | GCTTCCGATG | CAGGTGATTA | CACCCTGATC | GAAGCAGACG | 240
| CACTCGACTA | CACCTCCACC | TGCCCAGAAT | GCTCCCAACC | TGGGGTGTTT | CGTCATCACA | 300
| CCCACCGGAT | GCTCATTGAT | TTACCCATCG | TCGGGTTTCC | CACCAAACTG | TTTATCCGTC | 360
| TACCTCGCTA | CCGCTGCACC | AACCCCACAT | GTAAGCAAAA | GTATTTCCAA | GCAGAACTAA | 420
| GCTGCGCTGA | CCACGGTAAA | AAGGTCACCC | ACCGGGTCAC | CCGCTGGATT | TTACAACGCC | 480
| TTGCTATTGA | CCGGATGAGT | GTTCACGCAA | CCGCGAAAGC | ACTTGGGCTA | GGGTGGGATT | 540
| TAACCTGCCA | ACTAGCCCTC | GATATGTGCC | GTGAGCTGGT | CTATAACGAT | CCTCACCATC | 600
| TTGATGGAGT | GTATGTCATT | GGGGTGGATG | AGCATAAGTG | GTCACATAAT | AGGGCTAAGC | 660
| ATGGTGATGG | GTTTGTCACC | GTGATTGTCG | ATATGACCGG | GCATCGGTAT | GACTCACGGT | 720
| GTCCTGCCCG | GTTATTAGAT | GTCGTCCCAG | GTCGTAGTGC | TGATGCTTTA | CGGTCCTGGC | 780
| TTGGCTCCCG | CGGTGAACAG | TTCCGCAATC | AGATACGGAT | CGTGTCCATG | GATGGATTCC | 840
| AAGGCTACGC | CACAGCAAGT | AAAGAACTCA | TTCCTTCTGC | TCGTCGCGTG | ATGGATCCAT | 900
| TCCATGTTGT | GCGGCTTGCT | GGTGACAAGC | TCACCGCCTG | CCGGCAACGC | CTCCAGCGGG | 960
| AGAAATACCA | GCGTCGTGGT | TTAAGCCAGG | ATCCGTTGTA | TAAAAACCGG | AAGACCTTGT | 1020
| TGACCACGCA | CAAGTGGTTG | AGTCCTCGTC | AGCAAGAAAG | CTTGGAGCAG | TTGTGGGCGT | 1080
| ATGACAAAGA | CTACGGGGCG | TTAAAGCTTG | CGTGGCTTGC | GTATCAGGCG | ATTATTGATT | 1140
| GTTATCAGAT | GGGTAATAAG | CGTGAAGCGA | AGAAGAAAAT | GCGGACCATT | ATTGATCAGC | 1200
| TTCGGGTGTT | GAAGGGGCCG | AATAAGGAAC | TCGCGCAGTT | GGGTCGTAGT | TTGTTTAAAC | 1260
| GACTTGGTGA | TGTGTTGGCG | TATTTCGATG | TTGGTGTCTC | CAACGGTCCG | GTCGAAGCGA | 1320
| TCAACGGACG | GTTGGAGCAT | TTGCGTGGGA | TTGCTCTAGG | TTTCCGTAAT | TTGAACCACT | 1380
| ACATTCTGCG | GTGCCTTATC | CATTCAGGGC | AGTTGGTCCA | TAAGATCAAT | GCACTCTAAA | 1440
| ACAGGAAGAG | CC | | | | | 1452

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:2:

GGCCCTTCCG GTTTTGGGGT ACATCA        26

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:3:

GGCTCTTCCT GTTTTAGAGT GCATTG                        26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:4:

GGCTCTTCCG TTTTTAGAGT GCATTG                        26

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:5:

GGCTCTTCCG TTGTTAGAGT GCATTG                        26

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:6:

GGACCTGACC CCCATTTG                                 18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:7:

GGGCCCGACC CCGATATG                                 18

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:8:

CAAAATCGGG GCCATCAACA                               20

(2) INFORMATION FOR SEQ ID NO:9:

(i) SEQUENCE CHARACTERISTICS:

(A) LENGTH: 20 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:9:

GAGGACAAAC TGCGGTTCTG    20

METHOD FOR ISOLATION OF INSERTION ELEMENTS FROM CORYNEFORM BACTERIA

BACKGROUND AND INTRODUCTION

The present invention relates to a method of locating insertion elements (IS elements) or transposons in coryneform bacteria, a positive selection system suitable for the above, the IS elements found in this manner and their use.

Insertion elements (IS elements) are DNA which range from approximately 0.6 to 1.8 kilobases (kb) long and which can jump (transpose) in procaryotic genomes within a replicon or from one replicon to another (Craig & Kleckner 1987, in Neidhardt et al., "*Escherichia coli and Salmonella typhimurium*" Cellular and Molecular Biology, pp 1054–1074, ASM Press, Washington, D.C.). This can result either in a conservative transposition (i.e., an element changes its position) or in a replicative transposition (i.e., in which only a copy of the element integrates at the new insertion site whereas the original remains at the old position). A fusion of the donor molecule and of the acceptor molecule can occur in replicative transposition (replicon fusion). This intermediary stage of the transposition can then be disintegrated again by means of a recombination of the copies of the IS elements located at the fusion points. However, the replicon fusion can be retained if there is a suitable selection for it. IS elements themselves are not equipped with a selectable marker, in contrast to the closely related transposons.

IS elements usually code only for a single gene product, the so-called transposase. This is a recombination protein which is read by one or two open reading frames of the insertion element and which carries out the transposition by means of so-called illegitimate recombination (i.e., independent of the recombination system of the host organism) at the inversely repetitive ends of the element.

During the transposition of insertion elements into a bacterial gene, the latter is usually destroyed; thus, a mutation is produced (Craig & Kleckner 1987). In addition, a disconnection of genes located further to the rear can occur due to polar effects, the interruption of the transcription of an operon by means of the integration into a front gene.

Endogenic insertion elements can contribute to the genetic instability of a natural or recombinant microorganism. In addition to insertions of IS elements, deletions of bordering regions or other rearrangements of DNA are produced thereby. It is also known that insertion elements can exert a negative influence on the stability of plasmids, especially under production conditions (Kumar et al., Trends Biotech. (1991), volume 9, pages 279–284). Insertion elements have already been demonstrated in a number of various bacterial genera. In Gram-positive bacteria, insertion elements are known in particular from the genera Bacillus, Staphylococcus, Streptococcus, Lactobacillus and Streptomyces.

Insertion elements from coryneform bacteria, especially those producing amino acids, have not yet been described in the art.

SUMMARY OF THE INVENTION

An object of the present invention is to provide a method of locating insertion elements in coryneform bacteria and the positive selection system associated therewith.

The present invention concerns a method of locating insertion elements (IS elements) or transposons in coryneform bacteria, and the investigation of these bacteria for the presence of such elements. The method involves:

(1) The construction of a non-self-transferrable vector which can be mobilized from an *E. coli* mobilizer strain and is composed of
 (a) a DNA segment containing a replicon functional in *E. coli*,
 (b) a second DNA segment containing the DNA fragment coding for the mobilizing function (Mob site containing the oriT),
 (c) a third DNA segment which recombines homologously in Gram-positive bacteria and/or contains a replicon functional in coryneform bacteria,
 (d) a DNA segment from *Bacillus subtilis* containing the sacB gene, (2) Transfer of this vector by means of conjugative transfer into a coryneform recipient strain, (3) Cultivation of the transconjugant containing the vector in a sucrose-containing nutrient medium (e.g., ~10%), and (4) Lysis of the sucrose-resistant clone, cleaving of the plasmid with restriction endonucleases and analysis of the fragments.

BRIEF DESCRIPTION OF THE DRAWINGS

The present invention will be further understood from a study of the drawings, wherein:

FIGS. 2/1 and 2/2 show the base sequence of DNA fragment ISCg1 (SEQ ID NO: 1).

DETAILED DESCRIPTION OF THE INVENTION

Figure 1:
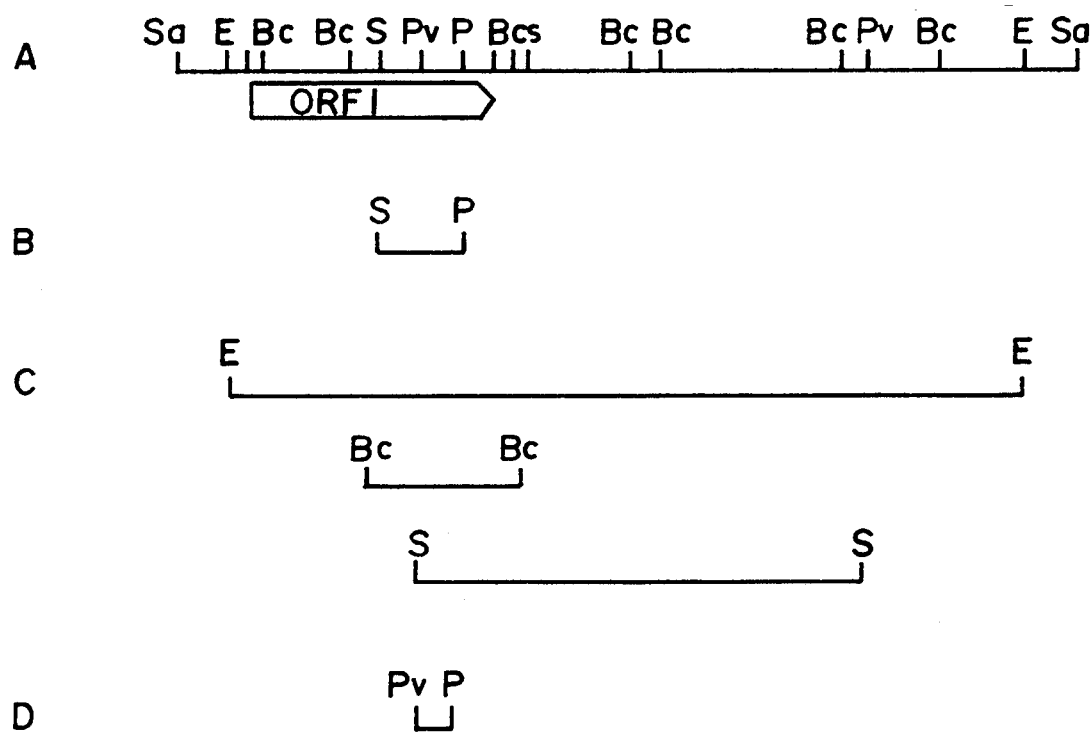
FIG. 1: (A) shows the restriction map of the 5.6 kb chromosomal Sau3A DNA fragment with the lysI coding region characterized as an arrow; (B) shows the 505 bp SstI-PstI DNA fragment used as hybridization probe; (C) shows the DNA fragments enlarged in mutant LT 5.5; and (D) shows the 283 bp PvuII-PstI DNA fragment on which the insertion was localized. Abbreviations: Bc=BclI; E=EcoRI; P=PstI; Pv=PvuII; S=SstI; Sa=Sau3A.

The construction of the suitable vectors (but not their effect as shuttle (catch) vectors) as well as the method for conjugative transfer is described in principle in DE-OS 38 41 453. The latter is characterized in that cells of Gram-positive bacteria are produced which are preferably restriction-defective and are mixed according to known crossing methods with an *E. coli* mobilizer strain carrying the mobilizable vector. The lack of an operable restriction system and the heat shock facilitate the transfer but are not a necessary prerequisite for it.

The stationary growth phase has proved to be favorable for the state of the recipient, whereas the donor is preferably in the logarithmic growth phase. Donor and recipient cells are generally used in a ratio of 1:1 to 1:10, preferably 1:1 to 1:6.

The suitable mobilizable vectors are not self-transferrable.

Point (1) above (i.e., construction of a non-self-transferrable vector which can be mobilized from an E. coli mobilizer strain) denotes in general all plasmids (vectors) which replicate independently in E. coli strains and which have proved to be useful according to the state of the art for genetic engineering applications. Examples of such E. coli vectors are pMB9, pBR322, pBR325, pKB111, pUC8, pUC9, pACYC184, pACYC177, and pSC101; customary E. coli vectors such as pBR325 (Bolivar, F., et al., Gene (1977), volume 2, page 95) or pACYC184 (Chang, A. C. Y., and Cohen, S. N., J. Bact. (1978), volume 134, page 1141) are neither self-transferrable nor sufficiently mobilizable.

These and other vectors which replicate only in bacteria strains of the E. coli group are modified by means of insertion of the Mob site of a plasmid with broad host range in Gram-negative bacteria. Plasmid RP4 is preferably used for these purposes. Such vectors, which carry an ~1.9 kb fragment (Mob site) from RP4, can be used with advantage in the method of the invention. Suitable mobilizer strains are modified E. coli strains containing a plasmid integrated in the chromosome or present in a free state which is capable of making available the functions necessary for mobilization. In particular, those strains are suitable in whose chromosome an RP4 derivative is integrated whose transfer function acts in trans on the Mob site of the above-named vectors.

Suitable vectors and E. coli mobilizer strains, such as SM-10, S68-7 and S17-1, are known from U.S. Pat. No. 4,626,504 (which is incorporated by reference in its entirety). The restriction defect facilitating the transfer can be genetically conditioned and generated for example by mutagenic agents (e.g. NTG: methylnitronitrosoguanidine); however, it can also be physiologically conditioned, for example by means of a heat shock. The heat treatment of the recipient directly prior to the crossing has proved to be especially effective; intact or spheroplasted cells should be used thereby. Surprisingly, this makes it possible for the first time to find insertion elements in Gram-positive bacteria in a purposeful fashion. The positive selection system (sacB system) used for this purpose for locating insertion elements in coryneform bacteria comprises a mobilizable, non-self-transferrable vector composed of:

(a) a DNA segment containing a replicon functional in E. coli, (b) a second DNA segment containing the DNA fragment coding for the mobilizing function (Mob site containing the oriT), (c) a third DNA segment which recombines homologously in Gram-positive bacteria and optionally contains a replicon functional in coryneform bacteria, and (d) a DNA segment containing the sacB gene and stemming from Bacillus subtilis.

The sacB gene from Bacillus subtilis is used for the isolation of insertion sequences (IS elements) or transposons in accordance with the invention (Gay et al., J. Bacteriol. (1983), volume 153, pages 1424–1431). The gene codes for the exoenzyme levan sucrase, which catalyzes the reactions of saccharose hydrolysis and levan synthesis (Dedonder et al., Methods in Enzymol. (1966), volume 8, pages 500–505). The expression of sacB in E. coli results in the transport of the enzyme into the periplasma (Steinmetz et al., Mol. Gen. Genet. (1983), volume 191, pages 138–144) and is lethal for E. coli and other Gram-negative bacteria placed on media containing over 5% sucrose (Gay et al., J. Bacteriol., volume 194, pages 918–921).

It was found that the expression of the intact sacB gene results in lethality on media with approximately 10% sucrose, even in Gram-positive bacteria such as C. glutamicum and other coryneform bacteria; sucrose concentration from over approximately 5% to approximately 10% can be utilized. Colonies with an inactivated sacB gene can therefore be positively selected on such media since in these instances the inactivation is brought about by insertion elements inserted in sacB. This is then localized by a restriction analysis.

Figure 3:
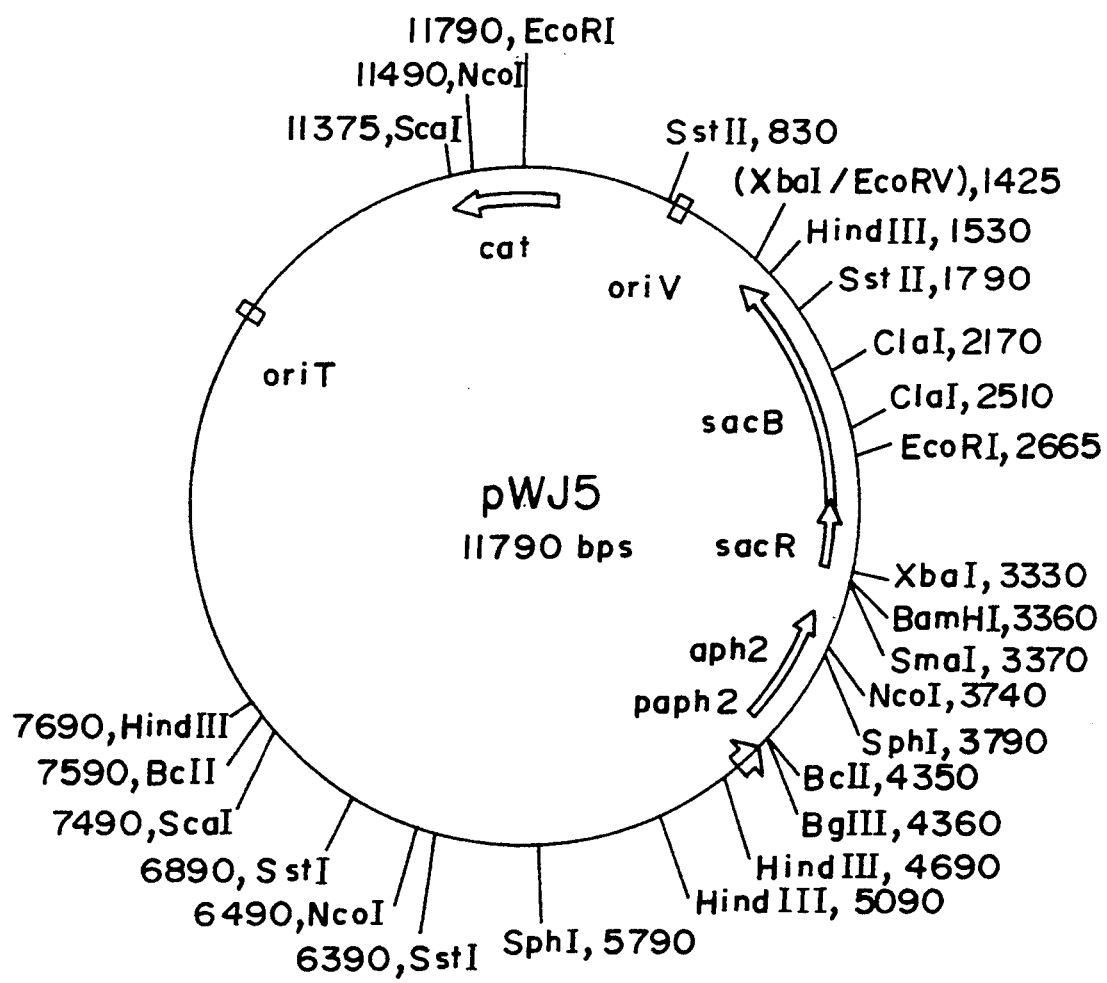
FIG. 3 shows the restriction map of shuttle (catch) vector pWJ5.

Shuttle (catch) vector pWJ5, whose restriction map is shown in FIG. 3 and which contains the sacB gene, is used with preference. It is derived from the plasmids pECM1 (DE-OS 38 41 453) and pUM24 (Ried and Collmer, Gene (1987), volume 57, pages 239–245).

After the restricting of plasmid pUM24 with the enzymes BamHI and EcoRV, an ~1.9 kb DNA fragment is produced which carries the sacB gene and is used with preference.

In this manner, three different IS elements obviously characteristic for the particular bacteria genera were found in a series of coryneform bacteria which are designated according to their origin as ISCg1, ISBl1 and ISRf1 (tables 1 and 2). The host range can extend beyond the genus of the bacteria in which the particular IS element was found. As a result of the hybridization of digoxygenin-d-UTP-marked DNA of IS elements which were identified in accordance with the method of the invention vis-à-vis e.g. total DNA from the microorganism to be investigated cleaved with EcoRI or another suitable endonuclease, any further copies of these IS elements present in the genome of this strain are then demonstrated.

Thus, the subject matter of the present invention particularly concerns the IS elements cited in table 2, for which the total length, the length IR and the length DR are especially characteristic. Naturally, bases can be replaced, in an equivalent manner in the sequences of the inversely repetitive ends without this altering the effectiveness, in a manner known to those skilled in the art. This also applies to the identified nucleotide sequence of ISCg1 (FIGS. 2/1, 2/2).

TABLE 1

Test of various coryneform bacteria for function of the sacB gene

| Strain with vector pWJ5 | Sensitivity to 10% sucrose | Occurrence of resistant clones | Insertions in pWJ5 |
|---|---|---|---|
| C. glutamicum | | | |
| ATCC 13032 | s | + | + |
| ATCC 13058 | s | + | − |
| ASO19 | s | + | + |
| C. herculis | s | + | + |
| C. acetoacidophilum | | | |
| ATCC 21350 | s | + | − |
| B. flavum ATCC 14067 | s | + | + |
| B. lactofermentum | | | |
| ATCC 13869 | s | + | + |
| B. divaricatum | | | |
| DSM20297 | s | + | − |
| R. fascians DM200-1 | s | + | + |
| R. fascians DM200-2 | s | + | + |

Abbreviations:
C. = Corynebacterium;
B = Brevibacterium;
R. = Rhodococcus.

TABLE 2

| | Properties of the IS elements found. | | |
| --- | --- | --- | --- |
| Name Organism | ISCg1 Corynebacterium glutamicum | ISBl1 Brevibacterium lactofermentum | ISRf1 Rhodococcus fascians |
| Total length | ~1,45 kb | ~1,45 kb | ~1,3 kb |
| IR length | 24 bp | 26 bp | 18 bp |
| DR length | 8 bp | 8 bp | 3 bp |
| Copies in host | 4–7 | 4 | 3 |
| Host range | C. herculis B. flavum R. fascians | | |

IR: Inversely repetitive ends
DR: Directly repetitive target site
kb: Kilobase pairs
bp: Base pairs
Sequences of the inversely repetitive ends *) **)
IR-L G G C c C T T C C g G T T T T g G g G T a C A T c a (SEQ ID NO:)
ISCg1
IR-R G G C t C T T C C t G T T T T a G a G T g C A T t g (SEQ ID NO:)
IR-L G G C T C T T C C G T T t T T A G A G T G C A T T G (SEQ ID NO: 4)
ISBl1
IR-R G G C T C T T C C G T T g T T A G A G T G C A T T G (SEQ ID NO:) 20
IR-1 G G a C C t G A C C C C c A T t T G (SEQ ID NO: 6)
ISRf1
IR-2 G G g C C c G A C C C C g A T a T G (SEQ ID NO: 7)
*): Lowercase letters symbolize non-homologous base pairs.
**): ISCg1 and ISBl1 exhibit approximately 75% sequence homology.

The action of an IS element can be demonstrated using a mutant of *Corynebacterium glutamicum* ATCC 13032. The *C. glutamicum* mutant LT 5.5 is a spontaneously S-(2-aminoethyl)-cysteine (AEC)-resistant mutant directly derived from the *C. glutamicum* wild-type strain ATCC 13032 and exhibiting a defect in the absorption of lysine. The lysI gene is the gene responsible in *C. glutamicum* for the absorption of lysine. This gene and the bordering DNA regions have been cloned and the nucleotide sequence of the lysI gene is known (Seep-Feldhaus, A.-H., Kalinowski, J. and Puhler, A., Mol. Microbiol. (1991), volume 5, pages 2005–3005).

If a 505 bp SstI-PstI DNA fragment marked with digoxygenin-d-UTP and from the lysI coding region is hydrolyzed via-à-vis total DNA from the *C. glutamicum* wild-type strain ATCC 13032 and from the mutant LT 5.5, a 5 kb EcoRI DNA fragment is found in the wild type whereas an approximately 6.5 kb EcoRI DNA fragment hybridizes in the mutant LT 5.5. The mutation in the lysI gene of mutant LT 5.5 can be traced according to this result to the insertion of an approximately 1.45 kb DNA fragment ISCg1, whose base sequence is shown in FIGS. 2/1 and 2/2. The presence of this IS element ISCg1 found in the classic manner can be corroborated with the aid of the method of the invention. At the same time, five IS elements are found in *C. glutamicum* ATCC 13032 which hybridize with digoxygenin-d-UTP-marked ISCg1-DNA and are therefore designated as IS elements of the type ISCg1.

A number of existing problems can be solved using the IS elements located in accordance with the method of the present invention:

The method, previously used in the case of bacteria, of producing mutageneses by means of chemicals has the disadvantage that often, in addition to the desired mutations, several other mutations are placed in a cell which could exert an unfavorable action. In addition, the mutated genes are not physically marked, since chemical agents usually effect point mutations (base exchange) under the conditions used.

Such a base exchange, or even several, are as a rule only suitable for disconnecting individual genes but not entire transcription units. Transposons and insertion elements offer a remedy in this connection in as far as generally only a single mutation event is produced per cell and a mutation produced in this manner is physically marked. This marking consists either in a selectable marker on the transposon or adjacent to an insertion element or, in the case of insertion elements not constructed in this manner, at least in a clear lengthening of the mutagenized range by means of a known sequence which can be identified by means of DNA hybridization.

The mutagenic activity of IS elements can be utilized by placing a selectable gene (e.g., an antibiotic-resistance gene) into or between two copies of an IS element by means of cloning in accordance with known methods. The (composite) transposon produced in this manner can be used for mutagenesis, in which instance the mutated gene is physically marked by the selectable gene. This broadens the area of application of transposon mutagenesis.

It develops in the detailed analysis of known *C. glutamicum* transposon mutants that in some instances even endogenic IS elements have changed their place in the genome of *C. glutamicum*. It then does not have to be unambiguously determined whether the transposon or insertion element produced the mutation to be observed phenotypically. Thus endogenic insertion elements can constitute a problem in transposon mutagenesis.

The method of the invention permits the rapid identification of IS elements and a determination by means of DNA hybridization vis-à-vis the total DNA in a transposon mutant strain of whether the insertion element pattern has been changed and there is the confirmation that the observed mutation was initiated by an insertion element.

Likewise, the complete removal of endogenic insertion elements by gene-replacement techniques assures a strain free of insertion elements in which strain phenotypic mutations can be associated unambiguously with the inserted transposon. Strains free of IS elements which are more suited for transposon mutagenesis can be found by using the identified insertion elements as hybridizing probes or by using the sacB technique for the identification of IS elements. Under optimum growth conditions the transposition rate of IS elements is usually below $1 \times 10^{-7}$ per generation; it is distinctly increased if the microorganism is placed under stress by means of changes of the external environment or by destabilization of the inner metabolic equilibrium. External stress factors are represented for example by heat, cold, lack of nutrients or antibiotic substances such as amino-acid analogues (Craig & Kleckner 1987).

Precisely for this reason, recombinant microorganisms or auxotrophic mutants or high production mutants exhibit a destabilized inner environment and are exposed for this reason to an elevated transposition frequency.

This mechanism can also be utilized in a positive fashion: Through introduction of the insertion elements found in accordance with the method of the invention, for example, DNA bordering regions can be multiplied.

The IS elements can also be used for mutagenesis by means of replicon fusion. Here the replicon fusion and therewith the mutation produced by means of selection of this fusion is stabilized. In the case of a fusion between the bacterial chromosome and a resistance plasmid carrying an IS element but not capable of replication, the resistance of the plasmid serves for the selection of the stable replicon fusion.

The instabilities in production strains can be significantly reduced under the conditions of production described above by means of the removal of endogenic IS elements in accordance with the method of the invention.

Mutagenesis and removal of endogenic IS elements begins in principle with the method known from DE 40 27 453 in which a mobilizable *E. coli* vector (like the one cited above having the distinguishing features 1(a–c), which, however, comprises as distinguishing feature (d) a DNA fragment containing the corresponding IS element), is transferred by conjugative transfer from an *E. coli* mobilizer strain into the desired coryneform bacterium.

EXAMPLES

Example 1

Mutation Initiation by IS Elements in *Corynebacterium glutamicum*: Demonstration and Isolation of an IS Element from the lysI Gene of the Mutant LT 5.5.

The *C. glutamicum* mutant LT 5.5 is a mutant derived directly from the *C. glutamicum* wild-type strain ATCC 13032, spontaneously resistant to S-(2-aminoethyl)-cysteine (AEC) and exhibiting a defect in the absorption of lysine. The lysI gene is the gene responsible in *C. glutamicum* for the absorption of lysine. The lysI gene and the bordering DNA regions have been cloned and the nucleotide sequence of lysI is known (Seep-Feldhaus, A. H., et al., Mol. Microbiol. (1991), volume 5, pages 2995–3005).

A 505 bp SstI-PstI DNA fragment marked with digoxygenin-d-UTP and from the lysI coding region (FIG. 1) was hybridized vis-à-vis the total DNA from the *C. glutamicum* wild-type strain ATCC 13032 and the mutant LT 5.5. The total DNA, isolated according to the method of Altenbuchner and Cullum (Mol. Gen. Genet. (1984), volume 195, pages 134–138), was cleaved for this purpose with the restriction enzyme EcoRI. The cleavage batches were subsequently separated in an 0.8% agarose gel. The transfer of the DNA fragments onto a nylon membrane (Hybond-N, Amersham, Braunschweig) took place according to the method of Southern (J. Mol. Biol. (1975), volume 98, pages 503–517). The hybridization was carried out with a "DNA Labeling and Detection Kit Nonradioactive" (Boehringer, Mannheim). The SstI-PstI DNA fragment used as hybridization probe hybridizes in *C. glutamicum* wild-type strain ATCC 13032 with a 5 kb EcoRI DNA fragment, whereas in mutant LT 5.5 an approximately 6.5 kb EcoRI DNA fragment hybridizes. The mutation in the lysI gene of mutant LT 5.5 can be traced according to this result to the insertion of an approximately 1.5 kb DNA fragment.

In order to determine the insertion site of the DNA fragment inserted into the lysI gene of mutant LT 5.5, the total DNA of *C. glutamicum* wild-type strain ATCC 13032 and of mutant LT 5.5 was cleaved in parallel with the restriction enzymes PvuII and SstI. The cleavage batches were subsequently separated in an 0.8% agarose gel. The transfer of the DNA fragments and the hybridization with the digoxygenin-d-UTP-marked SstI-PstI DNA fragment from the lysI coding region took place as described above. The hybridization shows that in mutant LT 5.5 both the 2.8 kb PvuII DNA fragment as well as the 0.9 kb SstI DNA fragment (FIG. 1) are lengthened by approximately 1.5 kb. It follows from the hybridizations that the insertion is localized on the 283 bp PvuII-PstI DNA fragment of the lysI coding region (FIG. 1).

For the cloning of the insertion the PvuII-PstI DNA fragment enlarged in mutant LT 5.5 was first amplified with the aid of polymerase chain reaction (PCR) (Innis, M. A., et. al., PCR Protokol, Academic Press, 1990). The primers used for the PCR reaction are oligonucleotides 20 bases long with the following sequences derived from the lysI DNA sequence:

Primer 1: 5' CAAAATCGGGGCCATCAACA 3' (SEQ ID NO: 8)

Primer 2: 5' GAGGACAAACTGCGGTTCTG 3' (SEQ ID NO: 9)

The PCR reaction was carried out with the following batch:

500 ng total DNA from the mutant LT 5.5,
14 ng primer 1,
14 ng primer 2,
200 μM d-NTP (dATP, dCTP, dGTP, dTTP),
dissolved in a volume of 50 μl Taq polymerase reaction buffer (Boehringer, Mannheim). The PCR reaction was carried out with the gene ATAQ Controller (Pharmacia). The batch was incubated at first for 5 minutes at 96° C. After the addition of 2.5 units Taq polymerase (Boehringer, Mannheim), the following cycle was run through 30 times for the amplification of the 1.8 kb PvuII-PstI DNA fragment:

1 minute 10 seconds at 53° C.,
2 minute 40 seconds at 72° C.,
1 minute 10 seconds at 92° C.

The amplified DNA was separated in a 0.8% agarose gel and isolated from the gel (Geneclean BIO101 Inc., La Jolla, Calif.). This DNA was cleaved with the restriction enzymes PstI and PvuII and ligated with the PstI- and SmaI-cleaved *E. coli* plasmid vector pK18mob (DE 40 27 453.5). The *E. coli* strain DH5α (Woodcock, D. M., et al., Nucleic Acids Res. (1989), volume 17, pages 3469–3478) was transformed with the ligation mixture. A plasmid called pSF3 was able to be isolated from the transformates, which plasmid consists of the vector pK18mob and of the 1.8 kb-long amplified DNA fragment.

Example 2

Sequence Analysis of the IS Element from *C. glutamicum*.

The approximately 1.8 kb DNA fragment from the *C. glutamicum* mutant LT 5.5 cloned in plasmid pSF3 (example 1) was sequenced according to the method of Sanger et. al. (Proc. Natl. Acad. Sci. USA (1977), volume 74, pages 5463–5467) with the modifications for the sequencing of double-stranded DNA (Chen and Seeburg, DNA (1985), volume 4, pages 165–168).

For this, deletion derivatives of plasmid pSF3 were produced by means of restriction mapping of certain cleavage sites. Since plasmid pK18mob is suitable for a direct sequencing, these deletion derivatives were able to be used immediately for sequencing.

The sequencing took place with the T7 sequencing kit (Pharmacia, Freiburg) and the "universal" and "reverse" primers. The nucleotide sequence was totally determined from both DNA strands (FIGS. 2/1 and 2/2).

The IS element ISCg1 is 1452 base pairs (bp) long and has imperfect inversely repetitive ends with a length of 24 bp. It produces a directly repetitive sequence of 8 bp at the insertion site in the lysI gene. It carries two open reading frames (ORF) which probably code for proteins. ORF1 (bp 130 to 417) codes for a protein of 96 amino acids and ORF2 (bp 321 to 1436) codes for a protein of 372 amino acids. ORF1 begins with an ATG start codon before which a sequence with a similarity to ribosome binding sites of Gram-positive bacteria is located (bp 117–121, 5'-AAAGG-3'). ORF2, which overlaps the end of ORF1, does comprise a few internal possible ATG- or GTG-start codons, but there are no visible ribosome binding sites located before them.

Example 3

Construction of a Vector for the Isolation of Insertion Sequences from Coryneform Bacteria.

The sacB gene from *Bacillus subtilis* is used for the isolation of insertion sequences (IS elements) or transposons (Gay et al., J. Bacteriol. (1983), volume 153, pages 1424–1431). The gene codes for the exoenzyme levan sucrase, which catalyses the reactions of saccharose hydrolysis and levan synthesis (Dedonder et al., Methods in Enzymol. (1966), volume 8, pages 500–505). The expression of sacB in *E. coli* results in the transport of the enzyme into the periplasma (Steinmetz et al., Mol. Gen. Genet. (1983), volume 191, pages 138–144) and is lethal for *E. coli* and other Gram-negative bacteria on media with over 5% sucrose (Gay et al, J. Bacteriol., volume 164, pages 913–921).

In this invention the sacB gene is used to locate insertion sequences in coryneform bacteria. The expression of the intact sacB gene also results in lethality for *C. glutamicum* and other coryneform bacteria grown on media containing 10% sucrose (example 4). Colonies with an inactivated sacB gene can therefore be positively selected on such media. This creates the possibility of locating insertion elements inserted in sacB. The IS shuttle (catch) vector pWJ5 (FIG. 3) is a derivative of plasmid pECM2. In order to produce plasmid pECM2, plasmid pECM1 (Schäfer et al., J. Bacteriol. (1990), volume 172, pages 1663–1666; EP 0,372,230) was cleaved with restriction enzyme SalI and religated with T4-DNA ligase. A derivative lacking the 0.3 kb SalI fragment of pECM1 was obtained thereby and designated pECM2. The IS shuttle (catch) vector was produced as follows: Plasmid pUM24 (Ried and Collmer, Gene (1987), volume 57, pages 239–246) was restricted (cleaved) with restriction enzymes BamHI and EcoRV, which created a 1.9 kb DNA fragment carrying the sacB gene. Plasmid pECM2 was cleaved with restriction enzyme XbaI and subsequently treated with the Klenow polymerase enzyme in order to digest the projecting individual strand ends produced at the cleavage site (Maniatis et al., Molecular Cloning 1, 2nd ed., 5.42, 1989). The DNA treated in this manner was purified and concentrated by phenolization and alcohol precipitation and then cleaved with the restriction enzyme BamHI. Both batches were combined and ligated with T4 DNA ligase. Competent cells of *E. coli* strain S17-1 (Simon et al., Biotechnol. (1983), volume 1, pages 784–794) were transformed with the ligation mixture. The selection of transformed clones took place primarily on PA agar (17.5 g Penassey broth + 15 g agar made up into 1 liter medium) with 50 µg/ml chloramphenicol. Resistant colonies were subsequently tested by means of a parallel application onto LB medium with 10% sucrose for the successful cloning of the sacB gens, recognizable from the sensitive phenotype.

Example 4

Isolation of IS elements from Coryneform Bacteria

The demonstration and isolation of insertion elements from coryneform bacteria on a large scale succeeded by using the sacB system:

The mobilizable shuttle (catch) vector pWJ5 (example 3) was transferred by conjugation (DE-OS 38 41 453.8; Schäfer et al., J. Bacteriol. (1990), volume .172, pages 1663–1666) from the mobilizer strain *E. coli* S17-1 (Simon et al., Biotechnology (1983), volume 1, pages 784–794) into a total of 20 coryneform recipient strains from the genera Arthrobacter, Brevibacterium, Corynebacterium, Microbacterium and Rhodococcus (table 1). The presence of unchanged pWJ5 plasmids in the coryneform strains was verified by lysis of the transconjugants (Birnboim & Doly, Nucl. Acids Res. (1979), volume 7, pages 1513–1523), cleavage of the plasmids with the restriction endonucleases BamHI and SspI and analysis of the fragments in agarose gel. In subsequent tests, each of the 20 strains tested exhibited growth on LB medium with $Km_{25}$ but no growth on $LBKm_{25}$ medium with 10% sucrose (table 1). This sucrose sensitivity can be traced to the expression of the intact sacB gens on plasmid pWJ5 since strains with plasmid pECM2 (example 3) can grow on $LBKm_{25}$ with 10% sucrose. Individual colonies of the strains to be tested, and carrying pWJ5, were incubated in LB liquid medium until achievement of the logarithmic growth phase at 30° C. in an air agitator. Approximately $5 \times 10^9$ cells were subsequently harvested at a time by centrifugation for 10 min. at 3000 rpms, the pellet taken up in 1 ml LB medium and applied onto the surface of a 0.45 µm cellulose acetate filter (diameter 40 mm, Sartorius, Gottingen, FRG) placed on LB medium. After having been dried up, an incubation of the cells took place for 20 hours at 38.5° C. The filters were thereafter washed off with 1 ml LB medium and then 0.1 ml of the resulting undiluted suspension (and of the suspension diluted in a 1:10 proportion with LB medium) were plated out onto $LBKm_{25}$ agar containing 10% sucrose. After storage for 2–3 days at 30° C., sucrose-resistant colonies were able to be obtained for all coryneform bacterial strains at varying frequencies (table 1). For *Corynebacterium glutamicum*, $2.5 \times 10^5$ sucrose-resistant colonies per batch were obtained, corresponding to a frequency of $5 \times 10^{-5}$. Sixteen sucrose-resistant clones were investigated by way of example by lysis, restriction of the plasmids with the enzymes BamHI and SspI and subsequent agarose gel electrophoresis. In eight clones an approximately 1.45 kb lengthening of the sacB gene in plasmid pWJ5 was able to be demonstrated. All insertions exhibited recognition sites for the restriction endonucleases BamHI, BclI, NcoI, HindIII and DraI, which are also present in insertion element ISCg1 (example 2). All insertions tested hybridized with digoxygenin-dUTP-marked ISCg1 DNA.

With the aid of the IS shuttle (catch) vector, insertions of the ISCg1 type were also able to be isolated from *C. glutamicum* AS019, *C. fascians* DM200-2, *C. herculis* and *B. flavum* ATCC 14067 (table 1).

Moreover, a hybridization of EcoRI-cleaved chromosomal DNA of various coryneform strains was carried out with the digoxygenin-dUTP-marked 1.9 kb fragment from the PCR reaction (example 2). The hybridization shows that 5 copies of ISCg1 or of a very similar element occur both in *C. glutamicum* ATCC 13032 and in mutant LT5.5. Furthermore, ISCg1 or a very similar element was identified by hybridization in the strains *C. glutamicum* AS019 and *Brevibacterium flavum* DSM 20411. No copies of ISCg1 were able to be demonstrated by hybridization in *C. glutamicum* ATCC 13058, *C. acetoacidophilum* ATCC 21350, *Brevibacterium divaricatum* DSM 20297 and in *E. coli* K12. The results determined by hybridization are thus in agreement with the distribution of IS elements of the ISCg1 type in coryneform bacteria strains determined with the aid of the IS shuttle (catch) vector.

An insertion of another type was isolated from *B. lactofermentum* ATCC 13869 (table 1) and called ISBl1. This approximately 1.4 kb insertion was also located in the sacB gene of PWJ5 and exhibits only partial homology with ISCg1. Four copies of ISBl1 were demonstrated in the genome of this strain by means of the hybridization of digoxygenin-dUTP-marked ISBl1-DNA vis-à-vis EcoRI-cleaved total DNA from *B. lactofermentum* ATCC 13869.

Moreover, an approximately 1.3 kb insertion sequence was identified in *Rhodococcus fascians* DM200-2 (formerly *Corynebacterium fascians*) (table 1) and designated with ISRf1. Restriction analyses and hybridization studies exhibited only slight similarities with the ISCg1 family and with ISBl1. Three copies of ISRf1 were demonstrated in the genome of the strain by hybridization of digoxygenin-dUTP-marked ISRf1 DNA vis-à-vis PstI-cleaved total DNA from *R. fascians* DM200-2. A copy of ISRf1 was able to be localized on an endogenic plasmid of *R. fascians* DM200-2.

Essential properties of the three isolated IS element types from coryneform bacteria are collated in a comparative manner in table 2.

Example 5

Mutagenesis of Coryneform Strains by Means of the Use of Insertion Elements

The principle of mutagenesis with insertion elements is presented using the example of strain *C. glutamicum* ATCC 13058 and using IS element ISBl1 (example 4):

An insertion of ISBl1 in a 0.65 kb HindIII-ClaI fragment of the sacB gene was localized on pWJ5 by means of restriction analysis. A 2.05 kb fragment was released by means of restriction of the pWJ5::ISBl1 plasmid with the restriction endonucleases HindIII and ClaI and isolated after separation by means of agarose gel electrophoresis from the gel. To this end a narrow strip of the gel with the corresponding fragment was cut out and treated with 2.5–3 volumes of 6 molar sodium iodide solution. After 10 minutes incubation at 55° C. the DNA from the now molten gel was isolated with the aid of the GeneClean Kit (BIO101 Inc., La Jolla, Calif, U.S.A.) in accordance with the instructions of the manufacturer, and purified. The projecting individual strand ends of the fragment were subsequently filled with the Klenow polymerase enzyme.

Figure 4:
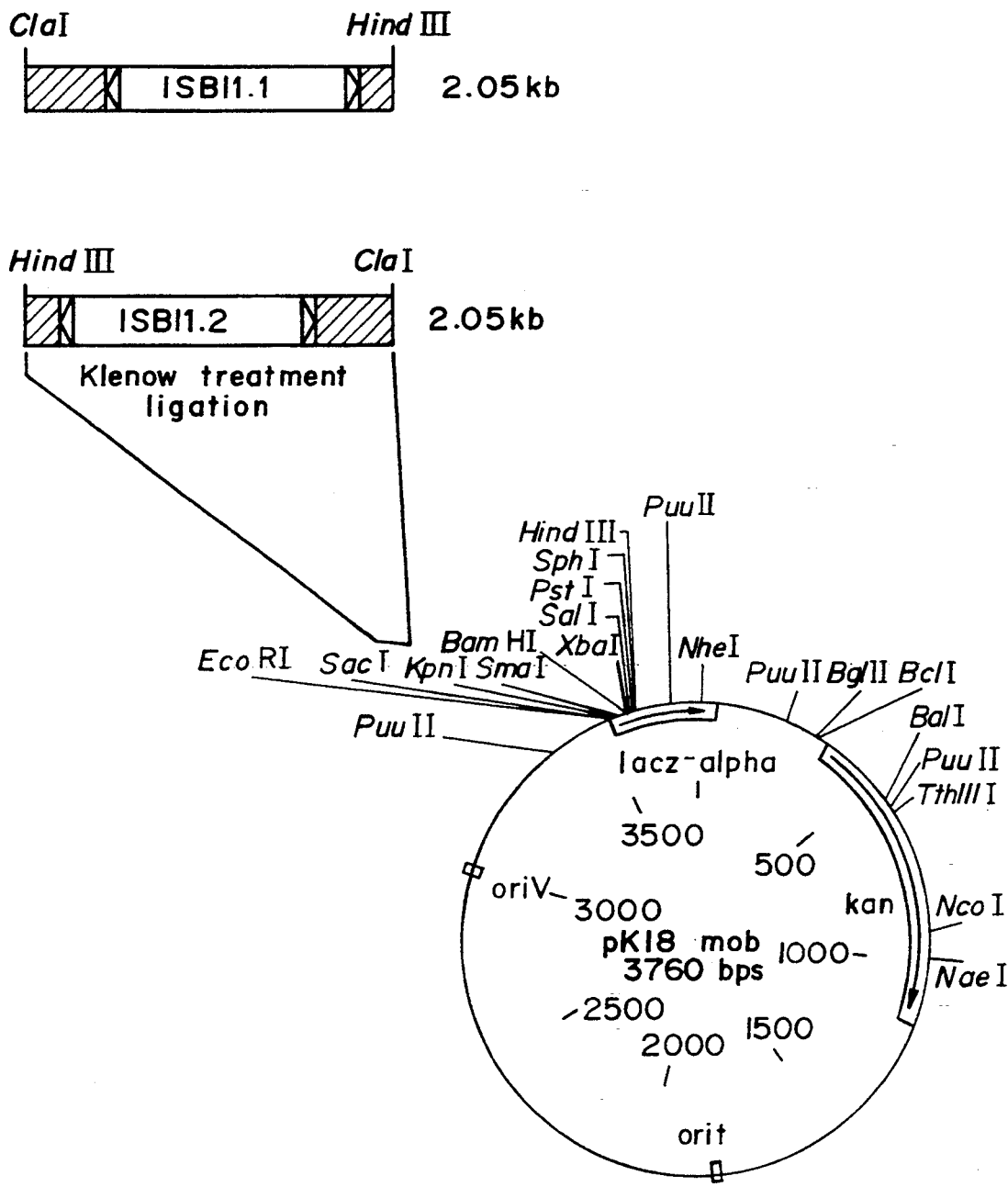
FIG. 4 shows construction of the vectors pK18mob::ISBl1.1 and pK18mob::ISBl1.2. Striped areas characterize parts of the sacB gene. The areas between the striped areas characterize the inverted repeats.

The mobilizable *E. coli* vector pK18mob (DE-OS 40 27 453) was linearized with the restriction enzyme SmaI and treated with the enzyme alkaline phosphatase in accordance with methods familiar to those skilled in the art (Maniatis et al., Molecular Cloning, 2nd ed., section 1.6, Cold Spring Harbor Laboratory Press, 1989). The vector treated in this manner was mixed with the filled HindIII-ClaI fragment and ligated with the enzyme T4 DNA ligase. The ligation batch was subsequently transformed into the *E. coli* strain Dh5α (Woodcock et al., Nucleic Acids Res. (1989), volume 17, pages 3469–3478). Transformants were plated out onto LB medium with kanamycin (50 µg/ml) and 5-bromo-4-chloro-3-indolyl-β-D-galactoside (20 µg/ml) and incubated for 24 hours at 37° C. White colonies were purified on LB medium with kanamycin (50 µg/ml) and the plasmid content analyzed by means of lysis of the cells, restriction of the plasmid DNA and agarose gel electrophoresis. Clones carrying the 2.05 kb insert with ISBl1 in both orientations were identified and designated with pK18mob::ISBl1.1 and pK18mob::ISBl1.2 (FIG. 4). pK18mob::ISBl1.1 was isolated from the strain *E. coli* Dh5α and transformed into competent cells of strain *E. coli* S17-1.

Plasmid pK18mob::ISBl1.1 was transferred from mobilizer strain *E. coli* S17-1 to *C. glutamicum* ATCC 13058 by conjugative transfer (Schäfer et al., J. Bacteriol. (1990), volume 172, pages 1663–1666; EP 0,372,230) at an incubation temperature raised to 38.5° C. 1500 transconjugants were obtained on selection medium (LBKm$_{25}$Nx$_{50}$). Twelve of these clones were tested by way of example for their plasmid content. No free plasmid DNA was demonstrated thereby. 400 transconjugants were inoculated in parallel onto LBKm$_{25}$Nx$_{50}$ and MMKm$_{25}$Nx$_{50}$ medium and incubated 2–3 days at 30° C. Three clones proved to be auxotrophic, since no growth on minimum medium could be observed. Twelve randomly selected transconjugant clones were cultivated in LBKms$_{50}$ medium and the total DNA isolated, cleaved with the EcoRI enzyme and separated in agarose gel. An integration of the vector was able to be verified at various sites into the genome of *C. glutamicum* ATCC 13058 by means of hybridization with digoxygenin-marked, EcoRI-cleaved pK18mob::ISBl1.1 DNA.

Further variations and modifications of the invention will become apparent to those skilled in the art from the foregoing and are intended to be encompassed by the claims appended hereto.

What is claimed:

1. A method of isolating an insertion element or transposon in coryneform bacteria, said method comprising:
   (a) constructing a non-self-transferrable vector mobilizable from an *E. coli* mobilizer strain, said vector comprising
      (i) a DNA segment containing a replicon functional in *E. coli*,
      (ii) a second DNA segment containing the DNA fragment coding for the Mob site containing the oriT,
      (iii) a third DNA segment which recombines homologously in Gram-positive bacteria and/or contains a replicon functional in coryneform bacteria, and
      (iv) a DNA segment from *Bacillus subtilis* containing the sacB gene,
   (b) transferring said vector by means of conjugative transfer into a coryneform recipient strain to form transconjugants,
   (c) cultivating said transconjugants containing said vector in a sucrose-containing nutrient medium to obtain sucrose-resistant clones, and
   (d) lysing said sucrose-resistant clones to obtain plasmids and cleaving said plasmids with restriction endonucleases to form fragments,
   (e) analyzing said fragments for the presence of an insertion element or transposon.

2. The method according to claim 1, wherein step (c) involves an approximately 10% sucrose-containing nutrient medium.

3. A positive selection system for locating an insertion element or transposon in coryneform bacteria, said system comprising a mobilizable, non-self-transferrable vector composed of:
   (a) a DNA segment containing a replicon functional in *E. coli*,
   (b) a second DNA segment containing the DNA fragment coding for the Mob site containing the oriT,
   (c) a third DNA segment which recombines homologously in Gram-positive bacteria and/or contains a replicon functional in coryneform bacteria, and
   (d) a DNA segment from *Bacillus subtilis* containing the sacB gene.

4. The selection system according to claim 3, wherein said vector is shuttle vector pWJ5 which is described by the restriction map of FIG. 3 and contains 11790 bp.

* * * * *